United States Patent [19]

Albiol

[11] Patent Number: 4,548,620
[45] Date of Patent: Oct. 22, 1985

[54] PROCESS FOR TREATING NATURAL GAS
[75] Inventor: Ignacio B. Albiol, Houston, Tex.
[73] Assignee: Key Engineering, Inc., Houston, Tex.
[21] Appl. No.: 577,776
[22] Filed: Feb. 7, 1984
[51] Int. Cl.⁴ .................................................. B01D 53/14
[52] U.S. Cl. ............................................ 55/48; 55/68; 55/73; 423/228
[58] Field of Search .................. 55/48, 51, 68, 73; 423/228, 229

[56] References Cited

U.S. PATENT DOCUMENTS

| | | | |
|---|---|---|---|
| 2,451,136 | 10/1948 | Wenzke | 55/48 |
| 2,943,703 | 7/1960 | Thayer | 55/51 |
| 3,824,766 | 7/1974 | Valentine et al. | 55/48 |
| 4,050,909 | 9/1977 | Ranke | 55/68 |
| 4,091,073 | 5/1978 | Winkler | 55/73 X |
| 4,332,596 | 6/1982 | Ranke et al. | 55/48 X |
| 4,370,156 | 1/1983 | Goddin et al. | 55/73 X |

Primary Examiner—Charles Hart
Attorney, Agent, or Firm—Lyman R. Lyon

[57] ABSTRACT

The disclosure relates to a process for treating sour natural gas by contacting the gas after it leaves an absorber with regenerated solvent permitting substantial reductions in capital cost, operating cost, energy consumption, and providing for a reduction of pollutants emitted to the atmosphere.

1 Claim, 2 Drawing Figures

PROCESS FOR TREATING NATURAL GAS

BACKGROUND OF THE INVENTION

This invention relates to the removal of acidic constituents such as carbon dioxide, hydrogen sulfide, and other sulfur compounds from natural gas. "Sweetening", as it is termed, is normally accomplished by an absorption process, with or without chemical reaction, using solutions of chemical or physical reactants, or combinations of both types of reactants. Most known processes are regenerative in nature and are based on the absorption-stripping principle.

More specifically, natural gas treatment or "sweetening" is generally accomplished by contacting the sour natural gas stream which may contain varying quantities of carbon dioxide, hydrogen sulfide and other sulfur compounds, with any one of a variety of known physical or chemical solvent reagents, or a combination of both, in an absorber. The solvent reacts chemically and/or absorbs acid fractions in the sour natural gas producing a marketable natural gas stream. The solvent is generally regenerated by flashing the acid gas therefrom by pressure reduction and/or heating the solvent to its boiling point in a stripper column. Solvent recovered from the regeneration system is cooled and recirculated back to the absorber column.

It is to be noted that absorption of acid molecules by either physical reactants or chemical solvents is exothermic in nature and, accordingly, the system temperature rises. As the system temperature increases the reaction rate slows, approaching an equilibrium condition. At a given temperature for each system the reaction stops and regeneration starts. Moreover, when the sweetening reaction slows, unreacted acid compounds may contaminate the system.

Another recognized problem is that the denuding of acid gas from the solvent in the solvent regeneration stripper is seldom complete and the residual acid components sometimes tie up as much as 20% of the reactive solvent, seriously reducing its effectiveness and/or requiring higher solvent circulation rates to accomplish the desired result. Thus, energy consumption for operating a gas sweetening unit is generally proportional to the solvent circulation rate.

In natural gas systems containing both carbon dioxide and hydrogen sulfide it is generally important that the amount of unreacted hydrogen sulfide be limited to a maximum of 4 ppm (parts per million) in the treated stream while the allowable carbon dioxide content may commonly reach 2,000 to 30,000 ppm in the system. Therefore, in order to denude the solvent to a point where essentially all of the hydrogen sulfide will be absorbed, excessive amounts of carbon dioxide must be first reacted and then regenerated to insure that essentially all of the hydrogen sulfide will be removed from the treated stream.

In most exothermic reactions an increase in temperature is detrimental to the reaction. Elevations in temperature of up to 30° to 40° F. are common in the absorber particularly in systems containing significant quantities of sour components. Such temperature increases in the sour system increase the corrosion rate. Also, the amount of energy required to regenerate the reagent rises significantly as the degree of regeneration increases. To overcome the potential negative effect of the higher system temperature excessive quantities of reagent are commonly circulated.

SUMMARY OF THE INVENTION

In order to minimize equipment costs, pumping costs, regeneration energy consumption, and inhibit corrosion products, the process of the instant invention utilizes a modified flow path as compared to natural gas sweetening processes currently known. By introducing regenerated solvent to the partially sweetening natural gas stream at a point upstream of the absorber, an immediate exothermic reaction or secondary absorption begins between any unabsorbed acid molecules and the solvent. The two streams are mixed, comingled and fed to a cooler to remove latent heat, sensible heat, heat of reaction and heat of absorption. Accordingly, the end contact temperature between the natural gas and solvent is relatively low. The cooling medium may be air, water, refrigerant or other fluids.

After any unabsorbed acid components of the natural gas and the solvent have reacted and are cooled, the mixture flows from the cooler to a separator where the sweetened gas is separated from the partially fouled solvent. The sweetened natural gas is then distributed to an end use and the solvent pumped back to the absorber for initial absorption of acid constituents from the raw or sour natural gas feed stock.

Since the temperature in the absorber is substantially reduced for any given specific quantity and quality of solvent and natural gas acid components, by the process of the instant invention, less solvent is required to accomplish the same degree of treatment compared to known treatment systems.

Computer model simulations of the instant invention indicate that the solvent circulation rate can be substantially reduced and regeneration heat energy reduced by 20% where the amount of carbon dioxide in the natural gas stream is the controlling factor. In the same system where the removal of hydrogen sulfide is the controlling factor, the regeneration heat requirement is reduced to 50% of conventional systems.

DETAILED DESCRIPTION OF THE PREFERRED EMBODIMENT OF THE INVENTION

Figure 2:
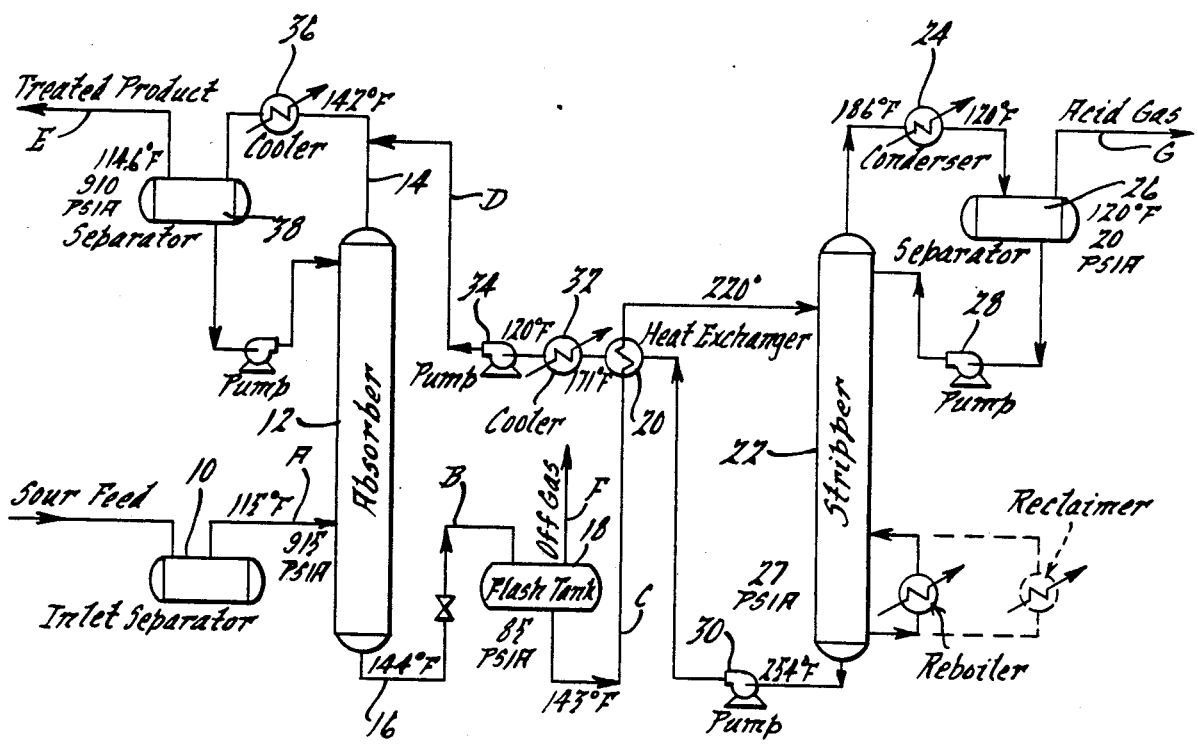
FIG. 2 is a view, similar to FIG. 1, wherein the hydrogen sulfide percentage limit is the controlling factor.

As best seen in FIG. 2 of the drawings, a process for removing acidic contaminants such as carbon dioxide, hydrogen sulfide, and other sulfur compounds from raw or sour natural gas termed "sweetening" comprises the steps of introducing sour natural gas feed stock to an inlet separator 10. Thereafter, carbon dioxide and hydrogen sulfide are removed from the sour gas stream by initially contacting the stream, at a temperature of 115° F. and pressure of 915 PSIA, with a known chemical or physical solvent, or a mixture of chemical and physical solvents, in a multistage countercurrent absorber 12. The initially treated natural gas stream leaves the top of the absorber 12 through a conduit 14 at a temperature of 135° F. and the fouled solvent leaves the bottom of the absorber 12 through a conduit 16 at a temperature of 156° F.

The fouled liquid solvent is then introduced at a relatively low pressure of 85 PSIA to a flash tank 18, the flashed vapor being removed from the system. The resultant degassed but fouled solvent is conducted from the flash tank 18 at a temperature of 155° F. to a heat exchanger 20 wherein its temperature is elevated from 155° F. to 220° F.

The fouled solvent is conducted from the heat exchanger 20 to a solvent regenerating stripper column 22 wherein carbon dioxide and hydrogen sulfide are removed. A carbon dioxide and hydrogen sulfide rich gas stream is conducted from the stripper column 22 at a temperature of 182° F. to a condenser 24, wherein the stream temperature is reduced to 120° F., thence to a separator 26. The resultant acid gas at 120° F. is then incinerated, directed to a sulfur producing plant, or used as feed stock to other chemical units. Condensate from the separator 26, at 20 PSIA, is conducted to a pump 28 thence to the top of the stripper column 22.

Stripped solvent at 254° F. is withdrawn from the bottom of the stripper 22 and is pressurized by a pump 30 to 27 PSIA for delivery to the heater exchanger 20, thence to a solvent cooler 32 at a temperature of 184° F.

In accordance with one feature of the instant invention, cooled solvent from the cooler 32 at 120° F. is pressurized by a pump 34 for introduction into the conduit 14 containing the initially treated natural gas stream emanating from the top of the absorber 12. Any residual acidic constituents in the initially treated natural gas stream are absorbed, further "sweetening" the resultant gas stream.

The mixed natural gas stream and partially fouled solvent stream, at a temperature of 135° F., are passed through a cooler 36 further lowering the temperature to 114.6° F. at a pressure of 910 PSIA facilitating further lowering of the carbon dioxide and hydrogen sulfide content in the resultant treated natural gas leaving the system.

The fully "sweetened" natural gas is discharged from the outlet separator 38, while the partially fouled solvent is conducted to the top of the absorber 12 for initial treatment of the acid molecules in the natural gas stream.

As seen in FIG. 2, the sweetening system is tuned to operate in a mode wherein the percentage limit of hydrogen sulfide is the controlling factor.

Use of the aforesaid two-stage sweetening process maximizes efficiency of the system in removing contaminants from the natural gas stream. Carbon dioxide, hydrogen sulfide and other sulfur compounds left in the stripped solvent leaving the solvent regenerating column 22 can be increased and/or the solvent circulation rate can be decreased while maintaining the same amount or less of carbon dioxide contaminant and/or lowering the amount of hydrogen sulfide in the treated natural gas stream. Any increase of contaminants in the solvent does not require a proportional increase in reflux of the solvent in the regenerating stripper thereby lowering the amount of energy required to strip the solvent. The lower reflux and stripper requirement reduces capital expenditures for equipment and materials.

A high degree of selectivity is achieved in removing hydrogen sulfide from the natural gas feed stock while permitting relatively high amounts of carbon dioxide in the treated natural gas. Moreover, while the solvent circulation rate may be reduced, a reduction in the reflux energy requirement and the energy required for solvent pumping and stripping is evidenced. A reduction in the size of equipment and materials heretofore used is also possible while maintaining the same or lower amounts of hydrogen sulfide in the treated natural gas. Selective removal of the amount of hydrogen sulfide from the sour feed stream requires less energy for incineration of the acid gas stream exiting the solvent regeneration stripper 22 and separator 26. The general reduction in system temperatures permits higher loadings of acid molecules in the solvent and permits higher concentrations of stripped solvents without increasing corrosion effects thereby reducing required water makeup. Power consumption of the solvent circulating pumps is also reduced.

The following Tables I, II and III reflect, respectively, the operating parameters of, a prior art system, a system of the instant invention wherein the carbon dioxide percentage limit in the treated gas is controlling, and a system of the instant invention where the hydrogen sulfide percentage limit in the treated gas is controlling.

TABLE I

| PRIOR ART STREAM FLOW RATE SUMMARY - LB - MOLES/HR | | | | | | | |
|---|---|---|---|---|---|---|---|
| STREAM | MDEA | NITROGEN | HYDROGEN SULFIDE | CARBON DIOXIDE | WATER | METHANE | ETHANE |
| A | — | 494.07 | 0.66 | 548.82 | 12.82 | 5547.57 | 5.28 |
| B | 867.22 | 0.25 | 0.82 | 455.61 | 5695.99 | 5.28 | 0.01 |
| C | 862.22 | 0.01 | 0.81 | 449.07 | 5695.33 | 0.23 | — |
| D | 862.22 | — | 0.17 | 5.28 | 5703.52 | — | — |
| E | — | 493.82 | 0.01 | 98.52 | 20.35 | 5542.29 | 5.27 |
| F | — | 0.24 | 0.01 | 6.54 | 0.66 | 5.04 | 0.01 |
| G | — | 0.01 | 0.64 | 443.76 | 41.86 | 0.23 | — |

Solvent Circulation: 400 Gallons/Minute
Heating Required: Stripper Reboiler Duty = 24.03 MMBTU/Hr.

TABLE II

Figure 1:
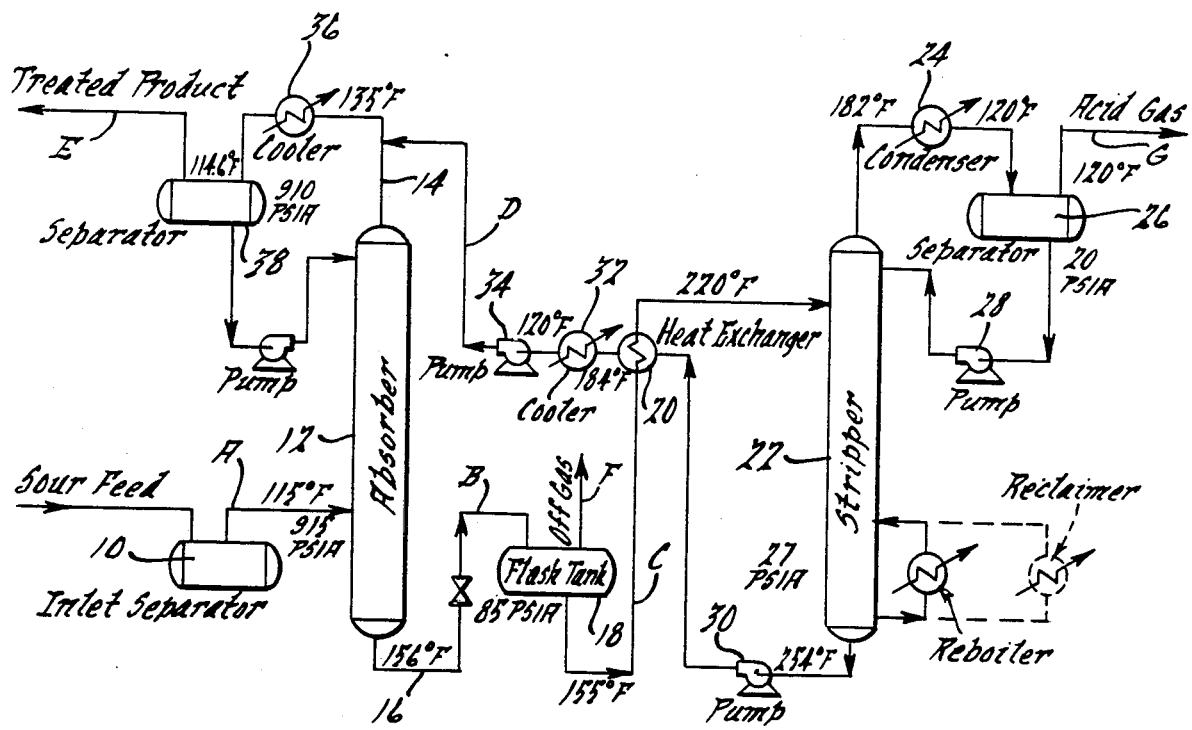
FIG. 1 is a schematic flow diagram of the natural gas treatment system of the instant invention, wherein the carbon dioxide percentage limit in the treated natural gas is the controlling factor.

| (SYSTEM OF FIG. 1) STREAM FLOW RATE SUMMARY - LB - MOLES/HR | | | | | | | |
|---|---|---|---|---|---|---|---|
| STREAM | MDEA | NITROGEN | HYDROGEN SULFIDE | CARBON DIOXIDE | WATER | METHANE | ETHANE |
| A | — | 494.07 | 0.66 | 548.82 | 12.82 | 5547.57 | 5.28 |
| B | 836.05 | 0.26 | 0.89 | 458.78 | 5534.77 | 5.27 | 0.01 |
| C | 836.05 | 0.01 | 0.88 | 454.72 | 5534.38 | 0.30 | — |

TABLE II-continued (SYSTEM OF FIG. 1)
STREAM FLOW RATE SUMMARY - LB - MOLES/HR

| STREAM | MDEA | NITROGEN | HYDROGEN SULFIDE | CARBON DIOXIDE | WATER | METHANE | ETHANE |
|---|---|---|---|---|---|---|---|
| D | 836.05 | — | 0.23 | 6.73 | 5530.35 | — | — |
| E | — | 493.81 | 0.01 | 96.76 | 8.40 | 5542.59 | 5.27 |
| F | — | 0.25 | 0.01 | 4.06 | 0.39 | 4.97 | 0.01 |
| G | — | 0.01 | 0.65 | 448.00 | 42.26 | 0.30 | — |

Solvent Circulation: 388 Gallons/Minute
Heating Required: Stripper Reboiler Duty = 20.04 MMBTU/Hr.

TABLE III (SYSTEM OF FIG. 2)
STREAM FLOW RATE SUMMARY - LB - MOLES/HR

| STREAM | MDEA | NITROGEN | HYDROGEN SULFIDE | CARBON DIOXIDE | WATER | METHANE | ETHANE |
|---|---|---|---|---|---|---|---|
| A | — | 494.07 | 0.66 | 548.82 | 12.82 | 5547.57 | 5.28 |
| B | 474.15 | 0.15 | 0.83 | 283.42 | 3140.74 | 3.11 | — |
| C | 474.15 | 0.01 | 0.83 | 281.49 | 3140.58 | 0.19 | — |
| D | 474.15 | — | 0.18 | 3.24 | 3136.44 | — | — |
| E | — | 493.92 | 0.01 | 268.65 | 8.52 | 5544.46 | 5.28 |
| F | — | 0.14 | 0.01 | 1.94 | 0.15 | 2.92 | — |
| G | — | 0.01 | 0.64 | 278.23 | 26.27 | 0.19 | — |

Solvent Circulation: 220 Gallons/Minute
Heating Required: Stripper Reboiler Duty = 12.43 MMBTU/Hr.

While the preferred embodiment of the invention has been disclosed, it should be appreciated that the invention is susceptible of modification without departing from the scope of the following claims.

I claim:

1. A process for removing acidic contaminants such as carbon dioxide, hydrogen sulfide, and other sulfur compounds from sour gas feed stock to effect sweetening thereof comprising the steps of removing carbon dioxide and hydrogen sulfide from the sour gas stream by contacting said stream at a first stage with an amine based chemical solvent in an absorber, regenerating the solvent by removing the carbon dioxide and hydrogen sulfide therefrom in a reboil stripper column, introducing the regenerated solvent under pressure to a partially sweetened gas stream emanating from the absorber at a second stage upstream of said absorber, cooling the mixed partially sweetened gas and solvent stream sufficiently so that the resultant overall rate of carbon dioxide pickup is substantially constant or lowered, while the rate of hydrogen sulfide pickup is maintained constant or increased thereby to effect a lowering of the energy requirements in said stripper column, separating the partially fouled solvent from the fully sweetened gas stream in an outlet separator, removing the fully sweetened gas from said separator, and introducing the partially fouled solvent to the absorber for contacting with the sour gas feed stock.

* * * * *